United States Patent [19]

Miyake et al.

[11] Patent Number: 5,446,536
[45] Date of Patent: Aug. 29, 1995

[54] SYSTEM OF DETECTING OPTICAL DISTORTION OF A LIGHT-TRANSMITTING PLATE-LIKE MEMBER

[75] Inventors: Atsushi Miyake, Hachiouji; Yoshimitsu Matsushita; Takayuki Koyama, both of Kawasaki, all of Japan

[73] Assignee: Nippon Sheet Glass Co., Ltd., Osaka, Japan

[21] Appl. No.: 55,149

[22] Filed: Apr. 30, 1993

[30] Foreign Application Priority Data

May 6, 1992 [JP] Japan .................................. 4-141001
Nov. 6, 1992 [JP] Japan .................................. 4-321396

[51] Int. Cl.⁶ .......................................... G01N 21/88
[52] U.S. Cl. .................................................. 356/239
[58] Field of Search ............... 356/237, 239, 430, 431; 250/572

[56] References Cited

U.S. PATENT DOCUMENTS

| | | | |
|---|---|---|---|
| 4,377,341 | 3/1983 | Task et al. | 356/239 |
| 4,398,822 | 8/1983 | Task | 356/239 |
| 4,461,570 | 7/1984 | Task et al. | 356/239 |
| 4,647,197 | 3/1987 | Kitaya et al. | 356/239 |
| 4,776,692 | 10/1988 | Kalawsky | 356/239 |
| 5,059,023 | 10/1991 | Task | 356/239 |

*Primary Examiner*—Vincent P. McGraw
*Attorney, Agent, or Firm*—Woodcock, Washburn, Kurtz, Mackiewicz & Norris

[57] ABSTRACT

When a predetermined region of a light-transmitting platelike member, such as a front windshield, is divided into a plurality of small parts to detect its optical distortion, and a target is sensed in turn through each small part of the region by image sensing means, according to one aspect of this invention, the target has at least three light emitting points capable of representing at least one angle, according to another aspect of this invention, the target represents at least two segments capable of forming at least one predetermined angle, and according to further aspect of this invention, a plurality of unit targets are arrayed in a predetermined direction, the image sensing means is swung along the above predetermined direction, and the platelike member is rotated in a direction across the predetermined direction.

24 Claims, 15 Drawing Sheets

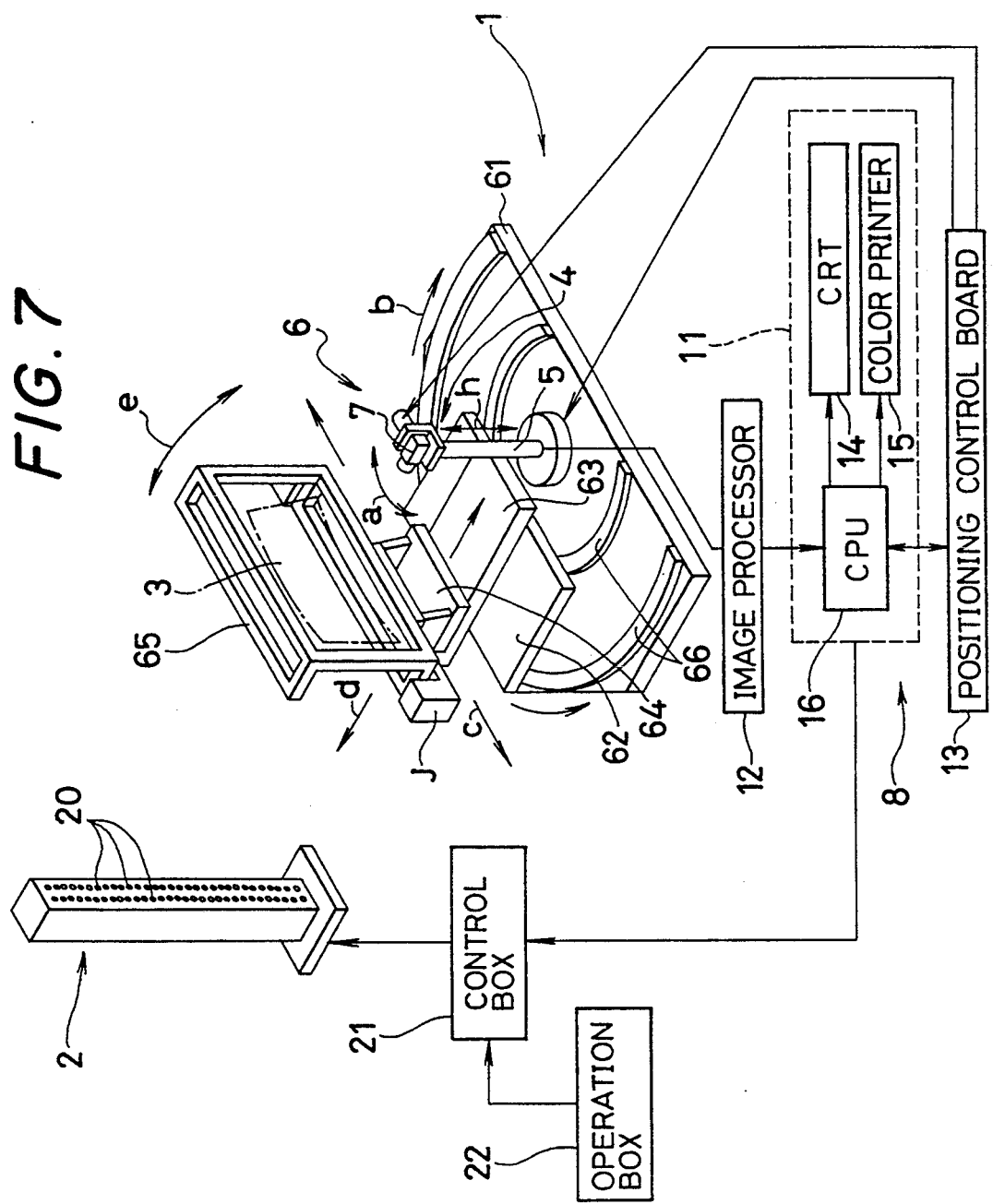

FIG. 14
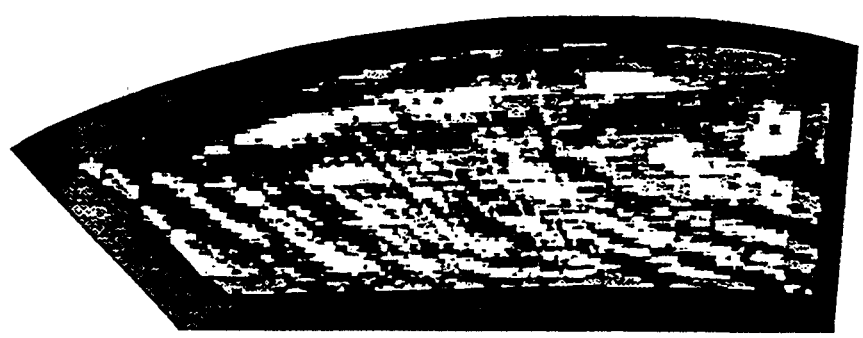
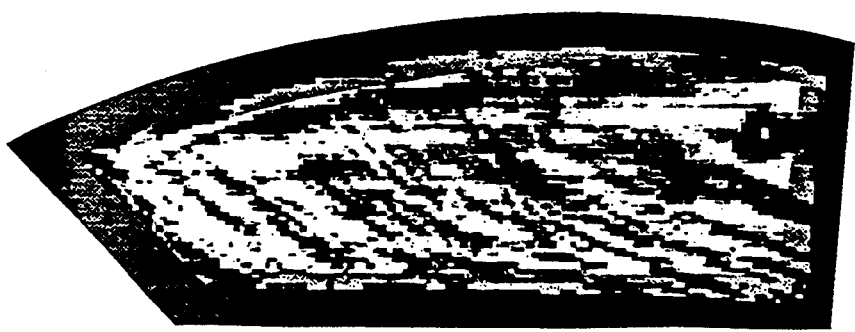

SYSTEM OF DETECTING OPTICAL DISTORTION OF A LIGHT-TRANSMITTING PLATE-LIKE MEMBER

BACKGROUND OF THE INVENTION

1. Field of the Invention

This invention relates to a system of detecting optical distortion of a light-transmitting platelike member, in which a predetermined region of the member is divided into a plurality of small parts and a target is sensed in turn through every small part of the region. The invention is particularly, but not exclusively, relates to a system of detecting optical distortion of a front windshield (front window glass) of a vehicle like an automobile.

2. Description of the Prior Art

Recently, the exterior design of an automobile has an inclination to give a complicated three-dimentional curved appearance to the automobile so as to fill aerodynamic requirements, so that the shape of a front windshield (hereinafter described simply as "windshield") has been improved so far. But it is difficult to maintain the surface of the windshield smooth because of a limit of glass forming technique. Accordingly, there are often such cases that an image viewed through the windshield is distorted when a driver sees an outside object. This phenomenon, referred to "optical distortion", is troublesome to the driver if the distortion reaches a certain level, and there is a possibility that the optical distortion obstructs a comfortable drive.

Qualitative evaluation of the optical distortion (which parts have positive lens effect and which parts have negative lens effect) can easily be done if a distribution of light parts and dark parts is examined in a projector photograph. The projector photograph is obtained in such a manner that light of a light source is projected on a screen through the windshield and an image of the windshield produced thereby on the screen is photographed.

When a glass plate is used as the windshield of the automobile, it is, however, necessary to know the optical distortion quantitatively in every part of the glass plate (divided into a plurality of small parts).

In a general way of managing the optical distortion quantitatively, the level of optical distortion is represented by two physical quantities: a lateral distortion angle, a distortion angle measured in a horizontal or lateral direction and a longitudinal distortion angle, a distortion angle measured in a vertical or longitudinal direction with each point of a platelike member such as the windshield. As shown in FIG. 1, the lateral distortion angle is defined by angle $\alpha$ formed by horizontal line AB with line A'B', which is observed when the line AB is viewed through the platelike member. The longitudinal distortion angle is defined by angle $\beta$ formed by vertical line AC with line A'C', which is observed when the line AC is viewed through the platelike member. The distortion angles $\alpha$ and $\beta$ are substantially in proportion to the amount of the optical distortion.

As another way of quantitatively managing the optical distortion, it is proposed to represent it with two physical quantities of elongation rates: a lateral elongation rate measured in a lateral direction and a longitudinal elongation rate measured in a longitudinal direction at every point of the platelike member, such as the windshield.

In FIG. 1, the lateral elongation rate PL is defined as a ratio ($PL = (L_2 - L_1)/L_1$) of a difference between length $L_1$ of horizontal segment AB and length $L_2$ of segment A'B', to length $L_1$, and the longitudinal elongation rate PH is defined as a ratio ($PH = (H_2 - H_1)/H_1$) of a difference between length $H_1$ of vertical segment AC and length $H_2$ of segment A'C', to length $H_1$. The elongation rates PL and PH are substantially in proportion to the amount of the optical distortion.

Shown in FIG. 2 is an illustration in which the distribution of light parts and dark parts represents the lens effect of the windshield. In FIG. 2, the light part corresponds to a region where a positive lens effect (the image of an object is enlarged in lateral, longitudinal or the other directions) was produced and the dark part corresponds to a region where a negative lens effect (the image of the object is contracted in lateral, longitudinal or the other directions) was produced.

According to an illustration shown in FIG. 2, it is, however, impossible to know the amount of the optical distortion quantitatively in every part of the windshield, so that it is difficult to precisely judge whether or not the optical distortion of such windshield raises problems when the windshield is applied to the automobile. Thus, it becomes necessary to examine lateral distortion angle $\alpha$ and longitudinal distortion angle $\beta$ in every point of the windshield.

Sometimes, there are such cases as to be impossible to precisely represent the optical distortion shown in FIG. 2 only with the lateral distortion angle $\alpha$ and longitudinal distortion angle $\beta$ shown in FIG. 1. The lateral distortion angle $\alpha$ and longitudinal distortion angle $\beta$ are produced only in parts of the windshield, in which the lens effect is not constant in the lateral or longitudinal direction. If the lens effect of the part of the windshield is invariably positive in the lateral direction and longitudinal direction, both lateral distortion angle $\alpha$ and longitudinal distortion angle $\beta$ are zero as shown in FIGS. 3A and 3B, whereas the lateral elongation is produced as shown in FIG. 3A, and the longitudinal elongation is produced as shown in FIG. 3B. Thus, if only the lateral distortion angle $\alpha$ and the longitudinal distortion angle $\beta$ are measured at that time, the measuring result leads to a misjudgment that no optical distortion is produced in the windshield, so that in addition to the measurement of lateral distortion angle $\alpha$ and longitudinal distortion angle $\beta$, it is sometimes preferable to measure lateral elongation rate PL and longitudinal elongation rate HL.

Makiguchi et al. research into a determination of "threshold distortion angle" which is an angle that man begins to feel the distortion, by means of combining actually detected distortion angles with sensory evaluation respecting the windshield of the automobile (Makiguchi et al., "*Analysis of optical distortion for automobile windshield glass*", the fifteen multivariate analysis symposium of Japan Science and Technology Association, November 1991). According to this research, it is proved that the threshold distortion angles differ with each of observation zones G1–G4 (FIG. 4) prescribed as test regions by the Japanese Industrial Standards (JIS) when the windshield 3 is observed from an eyepoint prescribed by JIS. Also, it has been made clear that the threshold distortion angles with each of the observation zones G1–G4 can be represented approximately by straight lines (discriminant functions) shown in FIG. 5, if the lateral distortion angle is given on the abscissa, and the vertical distortion angle is given on the ordinate.

In FIG. 5, a driver feels optical distortion if the distortion angles are on the upper sides of the lines that represent the discriminant functions respectively with the zones G1-G4 of the windshield 3, and does not feel any distortion on the lower sides thereof. In zones G1-G3 for example, if the lateral distortion angle is X° and the longitudinal distortion angle is Y° when light passes through each of the small regions of the zones, the driver feels optical distortion, but does not feel in zone G4. Accordingly, by utilizing the discriminant functions, it is possible to evaluate whether man-sensible optical distortion arises or not on the windshield 3, only by detecting the lateral and longitudinal distortion angles when the light passes through each of the many small regions of substantially overall area of the windshield 3.

However, according to Makiguchi et al., the optical distortion of the windshield 3 is detected, as shown in FIG. 6, in a state of mounting the windshield 3 actually on the automobile 9 and fixing a camera at the eye-point (the center of circle 10). The distortion is detected by taking a photograph of a panel 17 surrounding the automobile 9 and having a orthogonal lattice-like pattern, so that the following problems arise.

First, since the distortion angles, which are very little, should be read by man's eyes from the photograph, it takes very long time to be read but accuracy is not so good. Thus, exact detection can not be realized. Furthermore, it takes very long time to do such works as to mount the windshield 3 to the automobile 9, and to take, develop and enlarge photographs, so that it is not suitable for detecting the distortion with the many windshields 3. In addition, a large space is needed, since the panel 17 is large.

OBJECTS AND SUMMARY OF THE INVENTION

The present invention was made to solve the above problems, and it is an object of the invention to provide a system which can detect optical distortion of a platelike member in short time, also with high accuracy.

In accordance with one aspect of this invention, in a system of detecting optical distortion of a light-transmitting platelike member, in which a predetermined region of the member is divided into a plurality of small parts and a target is sensed in turn through each small part of the region, the system further comprises target means having at least one target that has at least three light emitting points capable of representing at least one predetermined angle; image sensing means for sensing the target through any of the small parts of the region; and position change means for changing a relationship of relative positions among the image sensing means, the target and the platelike member to alternate the small parts of the region, the small part being positioned between the image sensing means and the target sensed by the image sensing means, whereby the target is sensed by the image sensing means in turn through each small part of the region.

In preferred embodiments of this invention, the platelike member may be a front windshield of a vehicle, and the position change means may change the relationship of the relative positions in a state that the image sensing means is kept substantially constant in a position corresponding to an eye-point prescribed by the Japanese Industrial Standards for the vehicle. The predetermined angle represented by the three light emitting points of the target may be substantially a right angle. The target means may comprise a plurality of targets, each of which has at least three light emitting points, and when one target is being sensed by the image sensing means, only the light emitting points of the target to be sensed may be made to emit. The optical distortion may comprise at least one distortion angle with respect to at least one segment that is represented by at least three light emitting points. The at least one distortion angle may comprise a longitudinal distortion angle and a lateral distortion angle. The optical distortion may comprise at least one elongation rate with respect to at least one segment each represented by two of at least three light emitting points. At least one elongation rate may comprise a longitudinal elongation rate and a lateral elongation rate. The target may have four light-emitting points arrayed in the shape of a quadrilateral and at least one elongation rate may further comprises an elongation rate with respect to a segment extending in a diagonal direction. The optical distortion may comprise both the distortion angle and the elongation rate.

Moreover, in the system of this invention, processing means may be provided to control the change of the relative positions by the position change means, and to process image signals from the image sensing means in order to sense the optical distortion. The processing means may include means for converting the image signals into center coordinates specifying the at least three light emitting points, respectively.

In accordance with another aspect of this invention, in a system of detecting optical distortion of a light-transmitting platelike member, in which a predetermined region of the member is divided into a plurality of small parts and a target is sensed in turn through each part of the region, the system further comprises target means having a plurality of unit targets which are arrayed more in a predetermined direction than in a direction across the predetermined direction, and each of which can represent at least one predetermined angle; image sensing means for sensing the unit target through any of the small parts of the region; and position change means for locating every small part of the region, in turn, in a position between the image sensing means and the unit target, which is to be sensed by the image sensing means, by means of making the image sensing means swing substantially along the predetermined direction and the platelike member rotate along the direction across the predetermined direction, whereby the unit target is sensed by the image sensing means in turn through every small part of the region.

In preferred embodiments of this invention, the platelike member may be a front windshield of a vehicle, and the image sensing means may be made to swing on an axis substantially perpendicular to the predetermined direction and substantially through a position corresponding to an eye-point prescribed by the Japanese Industrial Standards for the vehicle, and the platelike member may be made to rotate on an axis substantially passing through the position corresponding to the eye-point and extending substantially in parallel with the predetermined direction. The unit target may comprise at least three light emitting points capable of representing at least one right angle substantially. Only a unit target to be sensed may be made to emit light when the image sensing means is put in action.

Moreover, the optical distortion may comprise at least one distortion angle with respect to at least one segment each represented by two of at least three light emitting points. At least one distortion angle may comprise a longitudinal distortion angle and a lateral distortion angle. The optical distortion may comprise at least one elongation rate with respect to at least one segment each represented by two of at least three light emitting points. At least one elongation rate may comprise a longitudinal elongation rate and a lateral elongation rate. The unit target may have four light-emitting points arrayed in the shape of a quadrilateral and the elongation rate may further comprise an elongation rate with respect to a segment extending in a diagonal direction. The optical distortion may comprise both the distortion angle and the elongation rate.

Further, in the system of this invention, processing means may be provided to control the swinging action of the image sensing means and the rotating action of the platelike member that are caused by the position change means, and to process image signals from the image sensing means in order to sense the optical distortion. The unit target may comprise at least three light emitting points capable of representing a right angle, and the processing means includes means for converting image signals into center coordinates respectively specifying the at least three light emitting points.

The above and other objects, features and advantages of this invention will be apparent from the following detailed description of illustrative embodiments thereof to be read in connection with the accompanying drawings, wherein like reference numerals identify the same or corresponding parts in the several views.

BRIEF DESCRIPTION OF THE DRAWINGS

FIG. 7 is a schematic general perspective view of a system of detecting optical distortion of a light-transmitting platelike member according to an embodiment of this invention;

FIG. 14 is a distribution representation of optical distortion of a windshield, represented with longitudinal distortion angles and lateral distortion angles;

DETAILED DESCRIPTION OF PREFERRED EMBODIMENTS

Figure 1:
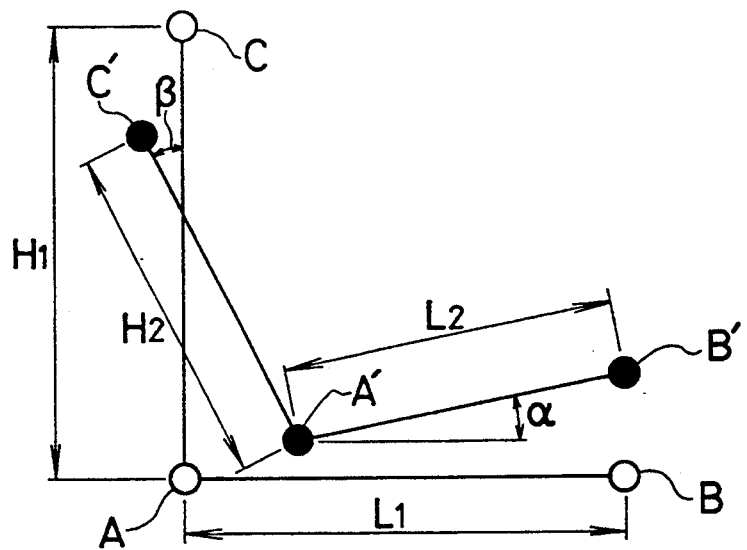
FIG. 1 is an explanatory Figure of definition of optical distortion produced when light passes through a platelike member.

Referring to FIGS. 7–17, systems of detecting optical distortion of a platelike member embodying the present invention will now be described in detail.

FIGS. 7–13 illustrate one of the embodiments and, particularly, FIG. 7 is a schematic general perspective view of the system.

Reference numeral 1 in FIG. 7 denotes, in whole, a system of detecting optical distortion of a windshield 3, a light-transmitting platelike member, of a vehicle like an automobile. The system 1 comprises a LED plate 2 that serves as target means, a CCD camera 4 that serves as image sensing means, and a mounting stand 6 that serves as position change means.

The LED plate 2 has many targets each comprising three light emitting spots, each of which is a light emitting diode (LED) 20. Almost all the windshield 3 is divided into a plurality of small parts, and the CCD camera 4 is arranged to sense the LED 20 through any one of a plurality of small parts. The small part may be of quadrilateral shape, particularly, of square shape, and its number is generally several thousands or tens of thousands.

To alternate the small part of the windshield 3 positioned between the CCD camera 4 and the target (comprising the three LEDs 20) to be sensed by the CCD camera 4, a relationship of relative positions among the CCD camera 4, the target and the windshield 3 is changed by the mounting stand 6. The mounting stand 6 holds the windshield 3 to enable it to rotate in a horizontal plane, and a pole 5 provided in the mounting stand 6 holds the CCD camera 4 to enable it to swing in a vertical plane.

In the embodiment, in which the optical distortion of the automotive windshield is detected, it is necessary to detect the optical distortion viewed from the driver, that is, viewed through the eye of the driver sitting in his predetermined seat. Thus, the CCD camera 4 swings upwards and downwards on an axis (which is hereinafter described as "the said horizontal axis") extending horizontally through a point 7 corresponding the eye-point prescribed in JIS for the automobile, and the windshield 3 rotates horizontally around an axis (which is hereinafter described as "the said vertical axis") extending upwards and downwards (vertically) through the point 7.

Figure 8A:
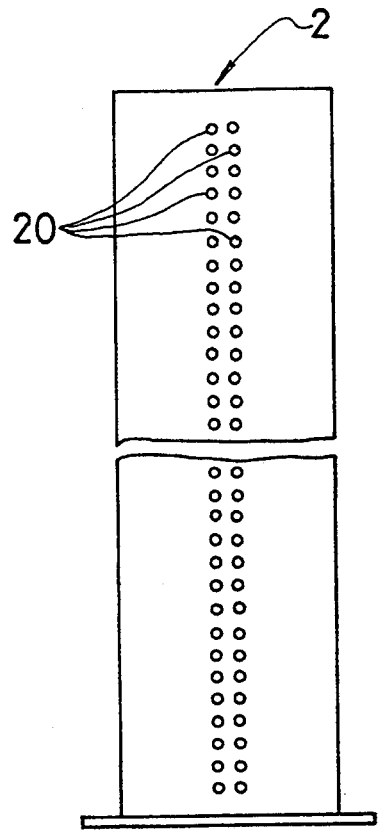
FIG. 8A is a front view presented by omitting an intermediate portion of the LED plate illustrated in FIG. 7.

Disposed as shown in FIG. 7 is the LED plate 2, a side of which has a plurality of LEDs 20 and faces the CCD camera 4. In the side of the LED plate 2, the LEDs 20 are arrayed vertically in two columns: in more detail, the LEDs 20 amounting to a total of 300 are divided into two columns as shown in FIG. 8A, and every pair of two adjacent LEDs 20 each belonging to the different columns keeps abreast with each other. Thus, the column comprises 150 LEDs 20.

The LEDs 20 are arranged on a lattice pattern and the interspace between the LEDs 20 is selected in a suitable length (preferably falling within a range of 10–100 mm). The position of each LED 20 is denoted by a pair of numerals (n, 1) or (n, 2). For example, denoted by (1, 1) is an LED 20 located in the uppermost left-hand position in FIG. 8A, in other wards, in the uppermost left-hand position when it is viewed from the CCD camera 4, and denoted by (1, 2) is an LED 20 located in the uppermost right-hand position in FIG. 8A. It is noted that "n" is a natural number of 1–150.

Figure 8B:
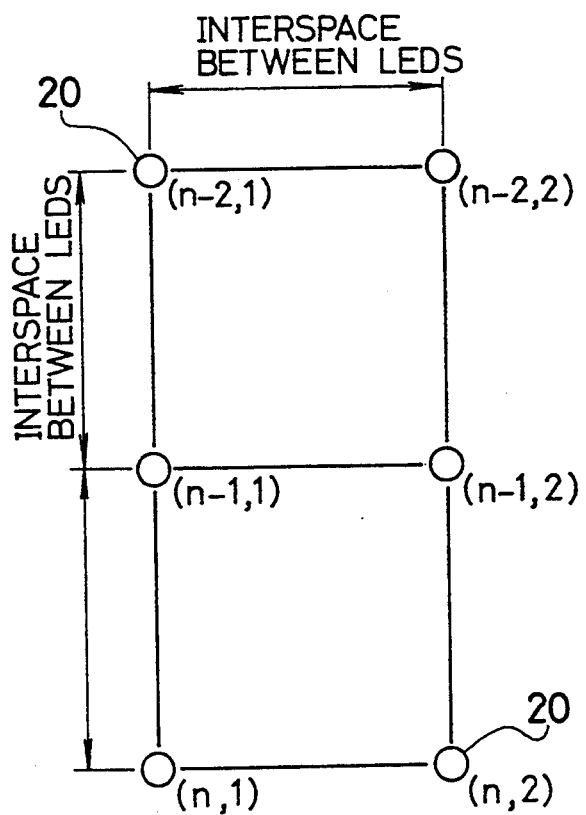
FIG. 8B is an enlarged fragmentary front view of the LED plate of FIG. 8A.

Lit at a time of photographing are only three LEDs 20 that represent a predetermined angle and are to be photographed with the CCD camera 4. Concretely, only three LEDs 20 located in positions (n, 1), (n, 2) and (n-1, 1) (n is a natural number of 2–150) in FIG. 8B are lit at the same time. In this embodiment, one target (unit target) consists of three emissive points (LEDs 20) that form substantially a right isosceles triangle, the number of the targets is 149 in a longitudinal direction and 1 in a lateral direction, and the targets longitudinally adjacent to each other hold an emissive point in common. But it is not necessary that the targets are arranged in one column. The targets may be arranged in two or more columns along the longitudinal direction. Furthermore, the targets may be arranged that each of (n, 1) LEDs 20 is not commonly hold.

The CCD camera 4 senses an image of three LEDs 20 arranged at (n, 1), (n, 2) and (n-1, 1) through one of the small regions, wherein substantially overall region of the windshield 3 is divided into small regions. The CCD camera 4 is supported by the pole 5 which is provided on the common base 61 of the mounting stand 6, so as to swing it (see arrow a in FIG. 7, hereinafter referred to "swing $\underline{a}$") on the horizontal axis along the vertical direction. The pole 5 provides a screw-operate mechanism (for example, rack-and-pinion mechanism (not shown)) for adjusting a height of the camera 4 in the range of between 100 and 500 mm from a lower side of the windshield 3 in the upper direction. Accordingly, the camera 4 can be adjustably supported at a point 7 corresponding to the eye-point of the automobile. The camera 4 swings in the range of between +40° and −20° with respect to the horizontal plane. In this embodiment, the CCD camera 4 is used for the image sensing means because of its easy operation and light weight. However, other image sensing means such as an industrial television (ITV) camera may be used.

The windshield 3 is supported by the mounting stand 6, so as to be rotatable (see arrow $\underline{b}$ in FIG. 7, hereinafter referred to "revolution $\underline{b}$") on the said vertical axis along the horizontal direction. Therefore while the rotation $\underline{b}$ is performed in connection with the swing $\underline{a}$, images of the target can be sensed by the CCD camera 4 through each of the small regions sequentially. The mounting stand 6 is assembled to allow the rotation $\underline{b}$ to be performed, and to be able to support the windshield 3 at the position matching with an actual design of the automobile on the basis of the point 7 corresponding to the eye-point.

The mounting stand 6 has two rails 66 on the common base 61 which are concentric with the said vertical axis, so as to rotate the windshield 3 in the horizontal direction on the said vertical axis. The rotating frame 62 which has rollers (not shown) on its lower surface and is rotatably mounted partially in the pole 5 is supported on the rails 66. A variable angle mechanism (not shown), such as a worm gear which is driven by a motor (not shown), is provided on a part of the rotating frame 62. Then, the rotating frame 62 rotates on the said vertical axis in proportion as the rollers rolls on the rails 66. Accordingly, the CCD camera 4 can always sense images of the targets through each of the small regions from the point 7 corresponding to the eye-point, wherever the rotating frame 62 is. The angle of the rotation $\underline{b}$ may vary in the range of between +70° and −70° with respect to a phantom line interconnecting the CCD camera 4 and the LED plate 2 each other at their center portion.

The mounting stand 6 comprises a transversely movable frame 63, a longitudinally movable frame 64 and a glass frame 65 on the rotating frame 62, in order to support the windshield 3 at the position matching with an actual design of the automobile on the basis of the point 7 which corresponds to the eye-point. A position of the windshield 3 in a left-right direction with respect to the said phantom line is adjusted by the transversely movable frame 63. A position of the windshield 3 in a longitudinal direction forwarding from the pole 5 to the LED plate 2 is adjusted by the longitudinally movable frame 64. A mounting angle of the windshield 3 with respect to the horizontal plane is adjusted by the glass frame 65.

For adjusting the position of the windshield 3 in the left-right direction, a handle (not shown) provided on the rotating frame 62 should be turned in a given direction. The transversely movable frame 63 then moves straightly (see arrow $\underline{c}$ in FIG. 7) along rails (not shown) on the rotating frame 62, because a screw-operate mechanism (not shown) is comprised between the rotating frame 62 and the transversely movable frame 63.

The transversely movable frame 63 may move 500 mm to each of the left and right side directions with respect to the said phantom line.

For adjusting the position of the windshield 3 in the longitudinal direction, another handle (not shown) provided on the transversely movable frame 63 should be turned in a given direction. The longitudinally movable frame 64 then moves straightly (see arrow $\underline{d}$ in FIG. 7) along rails (not shown) on the transversely movable frame 63, because a screw-operated mechanism (not shown) is provided between the transversely movable frame 63 and the longitudinally movable frame 64. Thus, the position of the windshield 3 is adjustable in the longitudinal direction and its adjustable range falls within 700–1600 mm if measured from the pole 5 to the LED plate 2.

To adjust the mounting angle of the windshield 3, an inclination handle (not shown) provided on the longitudinally movable frame 64 should be turned in a given direction. The glass frame 65 then rotates in a direction of arrow $\underline{e}$ on the axis J, because a variable angle mechanism such as a worm gear (not shown) is provided between the longitudinally movable frame 64 and the glass frame 65. The glass frame 65 may incline in the range of between 20° and 90° with respect to the horizontal plane. The windshield 3 may be attached to the glass frame 65 by some holders provided on the inner sides of the frame 65.

Above mentioned adjustments of the positions $\underline{c}$, $\underline{d}$ and the angle $\underline{e}$ may be performed by manually or automatically turning each of said three kinds of handles, before or after the windshield 3 is mounted to the mounting stand 6. When optical distortion of the windshield 3 is detected in practice, said positions $\underline{c}$, $\underline{d}$ and said angle $\underline{e}$ are fixed.

While optical distortion is detected, the swing $\underline{a}$ of the CCD camera 4 and the rotation $\underline{b}$ of the windshield 3 may be performed by manual operation. However, in this embodiment, the swing $\underline{a}$ and the rotation $\underline{b}$ is automatically performed as shown in FIG. 7 by utilizing a controlling and processing device 8 which includes two motors (not shown) for swinging the CCD camera 4 and rotating the windshield 3, respectively. The controlling and processing device 8 also automatically processes image signals from the CCD camera 4. This device 8 includes a personal computer 11 (having a color CRT display 14, a color printer 15 and a CPU 16), an image processor 12, a positioning control board 13 and the two motors for driving the windshield 3 and the camera 4, respectively.

The personal computer 11 gives orders for the swing $\underline{a}$ and the rotation $\underline{b}$ to the positioning control board 13. The positioning control board 13 drives the two motors on the orders. Then, the swing $\underline{a}$ of the camera 4 and the rotation $\underline{b}$ of the windshield 3 will be performed as mentioned above. An image signal from the CCD camera 4 is transmitted to the image processor 12. The image processor 12 converts the image signals to signals of respective center coordinates of the three light-emitting LEDs 20, where the center coordinates specify graphical central points of an area of the LED 20, in which its brightness exceeds a predetermined level. The converted signals are transmitted to the personal computer 11. The computer 11 calculates distortion angles and/or elongation rates of the small region through which the image was sensed on the basis of the converted signals. Data on the distortion angles and/or elongation rates are displayed in the CRT display 14 and printed by the printer 15. In short, the controlling and processing device 8 allows the swing $\underline{a}$ and the rotation $\underline{b}$ to be automatically and exactly controlled. Furthermore, the device 8 can promptly process the image signal and put out a result of the detection in a desired form, for example, through the display 14 and/or printer 15.

The system 1 may have a control box 21 and a operation box 22 as shown in FIG. 7. The LED plate 2, the personal computer 11 and the operation box 22 are connected to the control box 21. The control box 21 controls the on-off of all the LED plate 2 and, by means of changeover of a switch (not shown), controls which of the computer 11 or the operation box 22 switches on and off each LED 20.

When the operation box 22 switches on and off each LED 20, an optional LED 20 can be switched on and off by means of manually operating a digital switch (not shown) in the operation box 22. Accordingly, it is convenient for checking each LED 20 to operate each LED 20 as mentioned above.

If the computer 11 switches on and off each LED 20, the predetermined three LEDs are automatically switched on and off by the computer 11. Accordingly, it is preferable that the control box 21 is changed over as the computer 11 turns each LED 20 on and off when the detection of optical distortion is actually performed and, also in the embodiment, the detection of the optical distortion is performed in such state.

Figure 9:
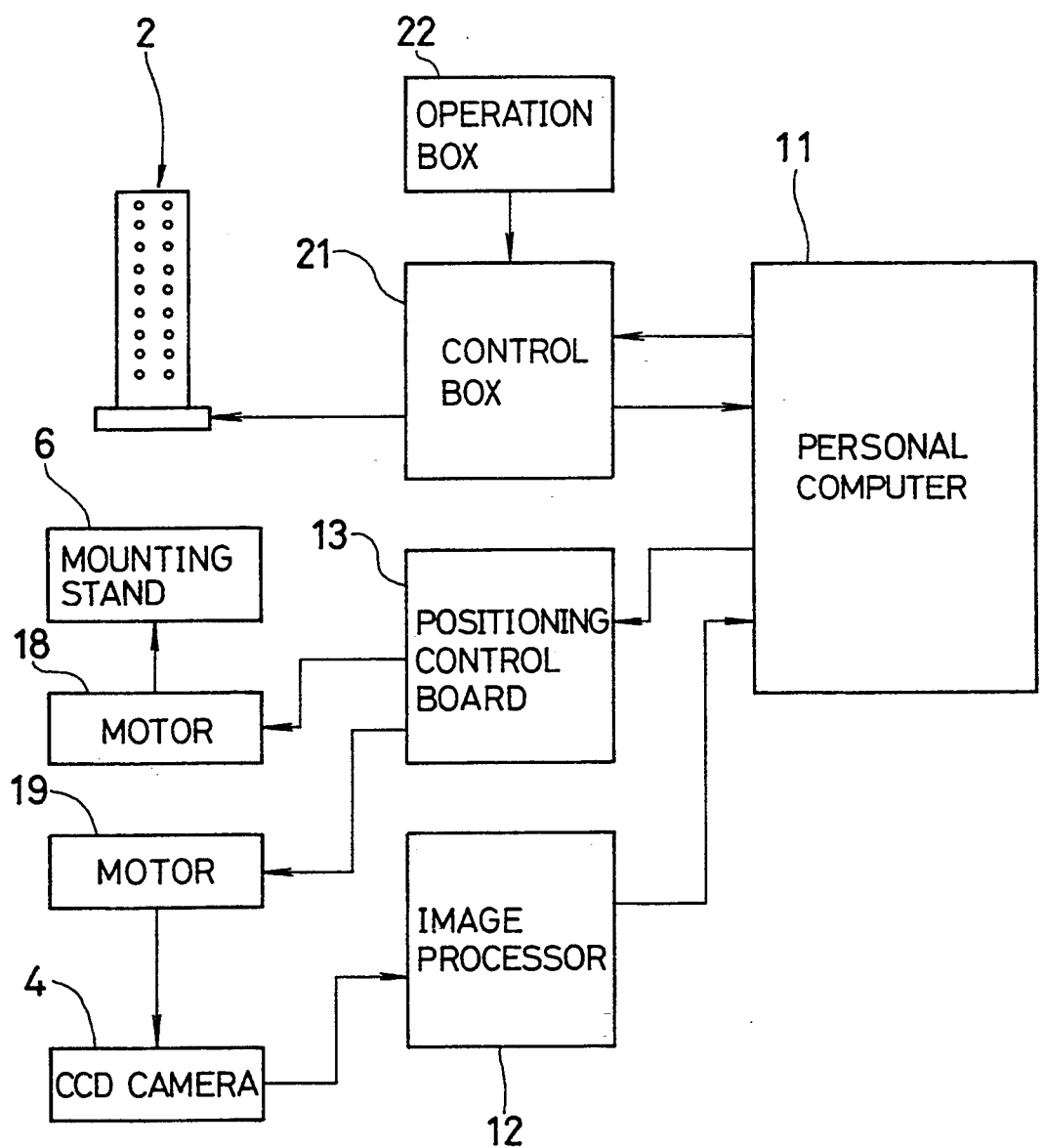
FIG. 9 is a block diagram of the system illustrated in FIG. 7.

Shown in FIG. 9 is a block diagram of a system 1 according to the embodiment of this invention. The control box 21, the image processor 12 and the positioning control board 13 are connected to the personal computer 11. In the event that the control box 21 is switched as the computer 11 automatically turns each LED 20 on and off, the control box 21 receives a 16 bit data signal indicating that which of groups of three LEDs 20 should be turned on, and turns on the three LEDs which are designated by the computer 11. The control box 21 also feeds back on, off and reset signals of each LED to the computer 11. The positioning control board 13 receives a signal for directing the swing $\underline{a}$ of the CCD camera 4 from the computer 11, and a signal for directing the rotation $\underline{b}$ of the windshield 3 from the computer 11. A sequencer and a motor controller included in the control board 13 drive the motors 18 and 19, which are previously mentioned, according to these signals. Then, the swing $\underline{a}$ of the camera 4 and the rotation $\underline{b}$ of the windshield 3 are performed within the predetermined angles. The image processor 12 converts each of image signals received from the CCD camera 4 to a signal which indicates center coordinates of each of the three LEDs 20, and transmits the converted signal to the computer 11. Above mentioned actions are managed solely by the CPU 16 (see FIG. 7) of the personal computer 11.

A procedure for actually detecting the optical distortion of the windshield of the automobile will be described below.

Figure 10:
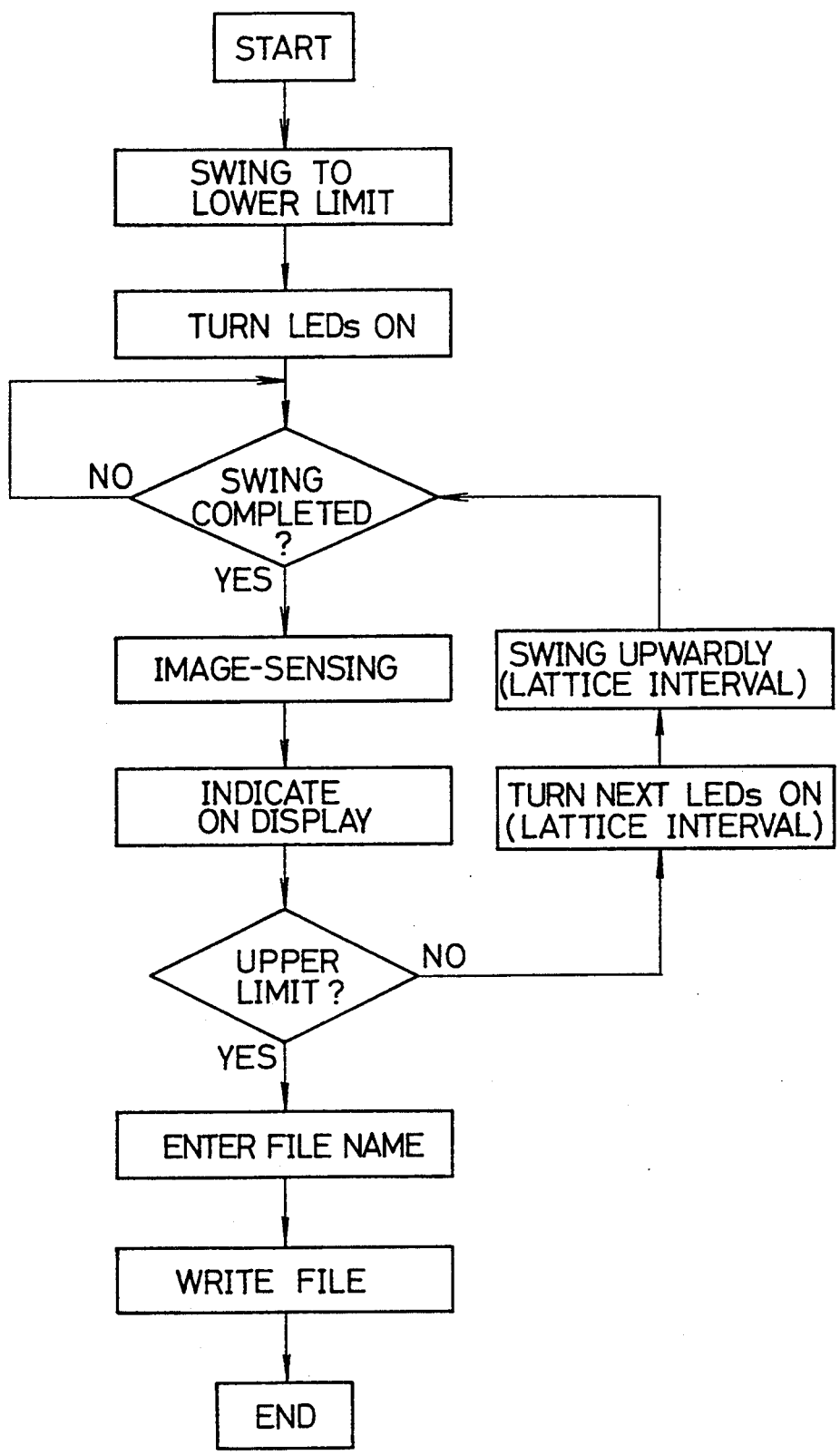
FIG. 10 is a flow chart of calibration measurement for the system of FIG. 7.

First, calibration measurement is performed under a condition that the windshield 3 is not mounted in the glass frame 65 of the mounting stand 6 as preparation for detecting optical distortion of the windshield 3, in order to obtain reference data for correcting mechanical errors with the LED plate 2, the mounting stand 6 etc. and for calculating optical distortion. A flow chart of the calibration measurement performed automatically by an order of the computer 11 is shown in FIG. 10.

At the first stage of the calibration measurement, the CCD camera 4 is swung (swing $\underline{a}$) as the three LEDs arranged at (150, 1), (150, 2) and (149, 1) come within the range of the camera 4. After these three LEDs are turned on and a completion of swing $\underline{a}$ is confirmed by the computer 11, said three LEDs are image-sensed. An image signal obtained by this image-sensing is transmitted to an image processor 12, and converted to signals which indicate center coordinates of each of the three LEDs. The converted signals are transmitted to the computer 11, and indicated in the CRT display 14.

At the next stage, two LEDs arranged at (150, 1) and (150, 2) are turned off, and at the same time two LEDs arranged at (148, 1) and (149, 2) are turned on. The CCD camera 4 is then swung (swing $\underline{a}$) upwardly at an angle corresponding to the lattice interval (the interspace between two adjacent LEDs 20), and three emitting LEDs arranged at (149, 1), (149, 2) and (148, 1) are image-sensed. This image signal is converted to signals of center coordinates, and the converted signals are indicated in the CRT display 14. The same actions are repeated 149 times until the three LEDs arranged at (2, 1), (2, 2) and (1, 1) are image-sensed. The calibration measurement is completed by filing data concerning to the converted signals to the computer 11.

If the windshield 3 belongs to such kinds of windshields that their optical distortion, such as the distortion angle and the elongation rate, has not been detected yet, it will become necessary for automatic detection by the controlling and process device 8 that the due range of the above optical distortion of the windshield 3 is previously determined. In that event, the windshield 3 is, firstly, secured to the glass frame 65 in accordance with a situation in an actual automobile. Secondly, both the range of the swing a (the swinging action) of the CCD camera 4 and the range of the rotation b (the rotating action) of the windshield 3 are determined under such secured state. It is to be noted that the above swinging range of the CCD camera 4 and the above rotating range of the windshield 3 must be determined in such a manner that the CCD camera 4 can be leveled in turn at all of the plurality of small parts, into which the windshield 3 is substantially divided.

Figure 11:
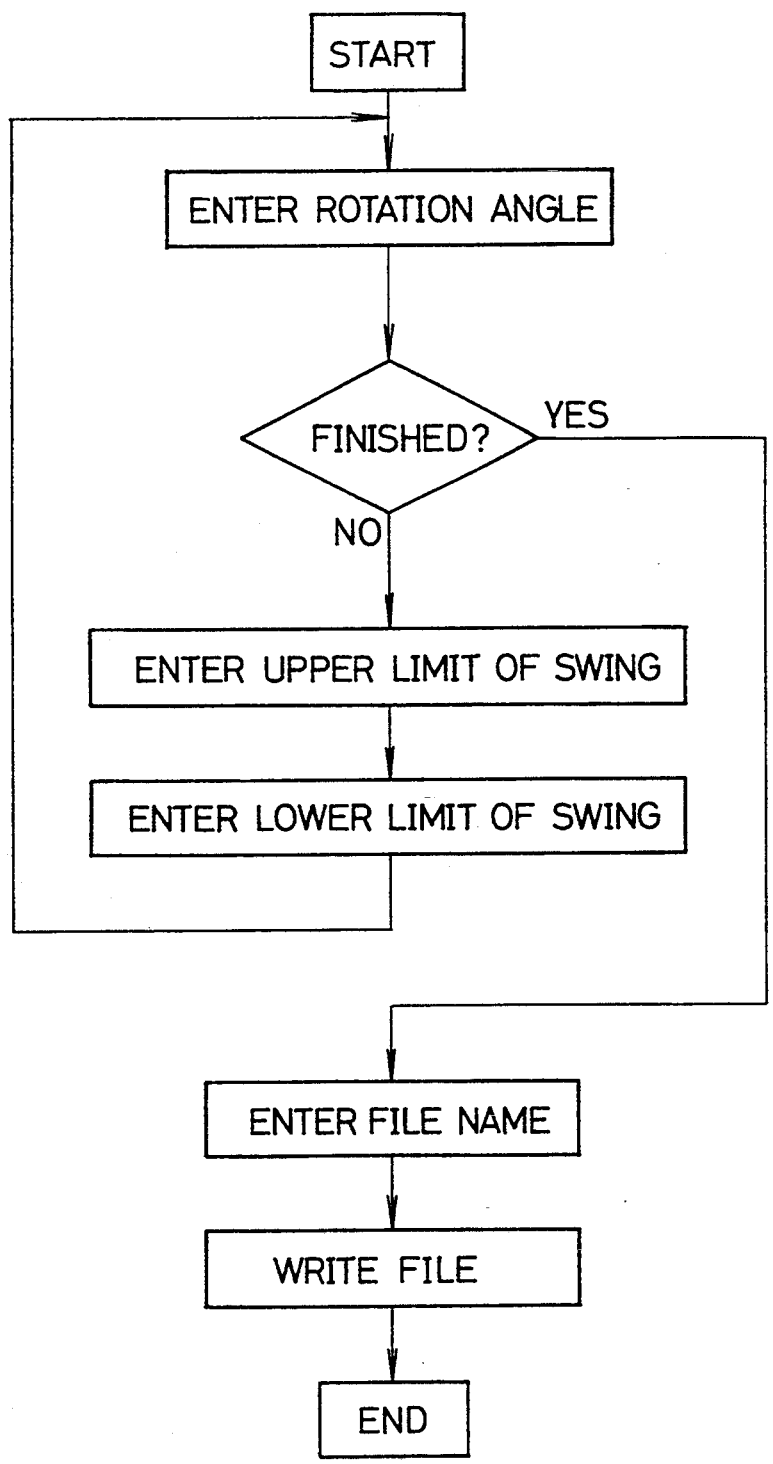
FIG. 11 is a flow chart showing progress of defining a detecting range for the system of FIG. 7.

A flow chart showing progress of defining the ranges of swing a and rotation b is shown in FIG. 11. In this measurement for the definition, the swing a and the rotation b is not performed automatically by an order from the computer 11, but performed manually.

At the first stage of this progress, the windshield 3 is mounted in the glass frame 65 of the mounting stand 6, in a position matching with an actual design of the automobile on the basis of the point 7 which corresponds to the eye-point. The windshield 3 is then manually rotated (rotation b) as a left end portion (viewing from the camera 4) of the windshield 3 comes within the range of the camera 4. An angle (hereinafter referred to "left limit angle") of the windshield 3 with respect to the said phantom line, which is previously set forth, is surveyed and entered to the computer 11.

Furthermore, an angle (hereinafter referred to "upper limit angle") of the camera 4 with respect to the horizontal plane on a condition that an uppermost small region comes within the range of the camera 4, and an angle (hereinafter referred to "lower limit angle") of the camera 4 with respect to the horizontal plane on a condition that an lowermost small region comes within the range of the camera are surveyed by manually swinging the camera 4 without rotating the windshield 3. These two angles are entered to the computer 11.

At the next stage, the windshield 3 is anticlockwisely rotated on the said vertical axis at an angle corresponding to the lattice interval. Then, while the angle of the rotation b is fixed, the upper limit angle and the lower limit angle are surveyed by manually swinging the camera 4 in the horizontal direction, and entered to the computer 11. The same actions are repeated until a right end portion of the windshield 3 comes within the range of the camera 4 (this angle is referred to "right limit angle") and the two angles of camera 4 are surveyed. The progress for the definition are completed by filing data of the detection ranges concerning the limit angles to the computer 11.

By utilizing the calibration data and the detection range data obtained by the above mentioned procedures, the optical distortion of the windshield 3 can be detected automatically.

Figure 12:
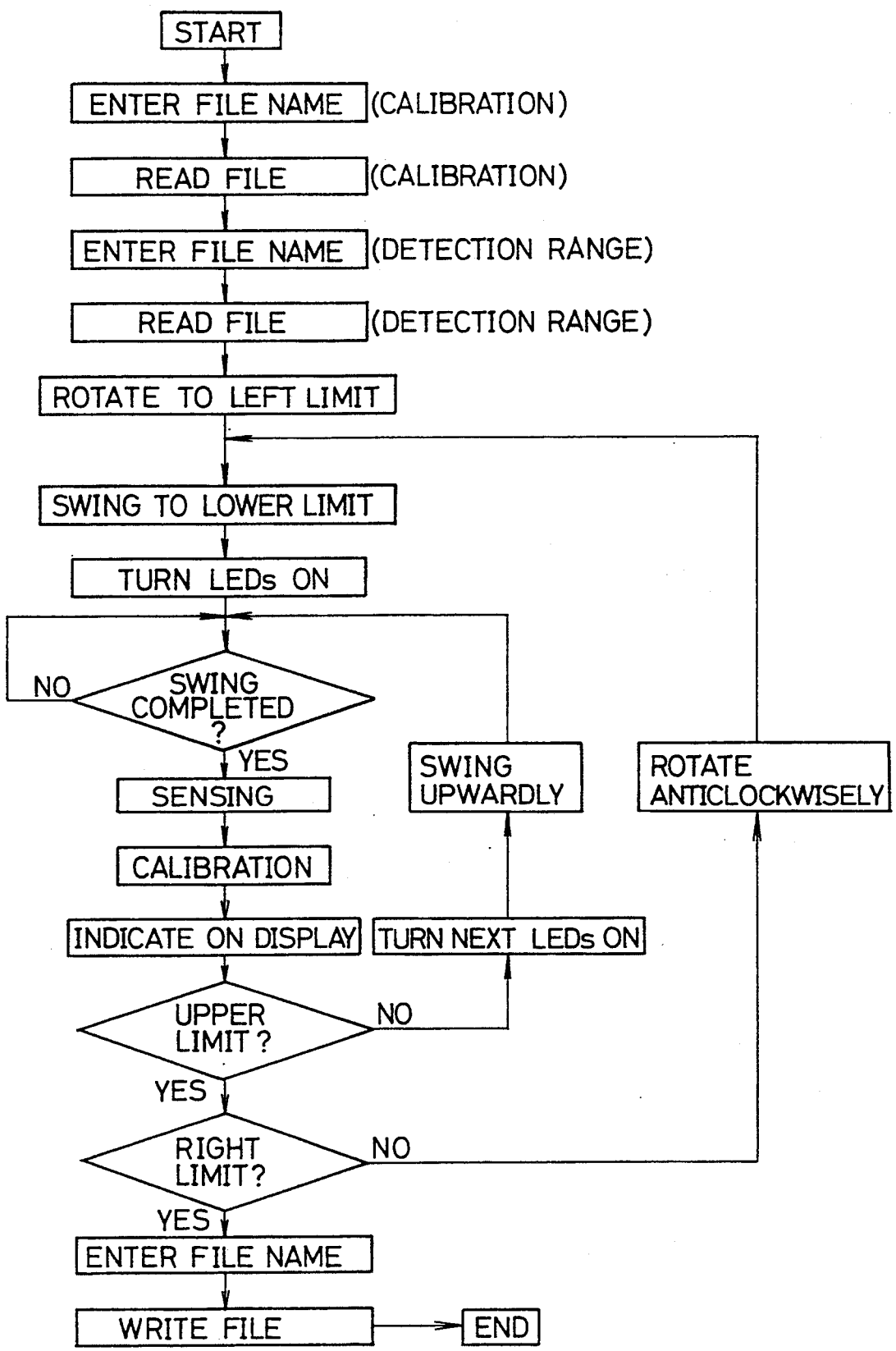
FIG. 12 is a flow chart showing progress of detecting optical distortion of a windshield for the system of FIG. 7.

A flow chart of showing progress of automatically detecting the optical distortion of the windshield 3 is shown in FIG. 12.

At the first stage, while the windshield 3 is mounted in the glass frame 65 according to the design of the automobile, a calibration file and a detection range file are read from a floppy disk of the personal computer 11. Then the windshield 3 is rotated (rotation b) to the left limit angle, and at the same time the camera 4 is swung (the swing a) to the lower limit angle at the left limit angle. Three LEDs 20 arranged at (n, 1), (n, 2) and (n-1, 1) which come within the range of the camera 4 are turned on by an order from the computer 11.

These three light-emitting LEDs are image-sensed by the CCD camera 4 through a small region which is at the left end and the lowermost portion of the windshield 3. An image signal is transmitted from the camera 4 to the image processor 12, and converted to signals which indicate the center coordinates of each LEDs. Then, the converted signals are sent to the computer 11, and the distortion angle and/or the elongation rate are calculated by comparison of the respective center coordinates, which are calibrated by using the calibration data, of the above three LEDs 20 with the calibration data, and displayed on the CRT display 14.

In that event, referring to FIG. 1, each optical distortion can be calculated as follows.

The lateral distortion angle will be obtained by calculating angle $\alpha$ that segment AB forms with segment A'B' which lies between the center coordinates A' and B' of two of the three LEDs 20, and the longitudinal distortion angle will be obtained by calculating angle $\beta$ that segment AC forms with segment A'C' which lies between the center coordinates A' and C' of two of the three LEDs 20.

Moreover, the longitudinal elongation rate PL will be obtained by calculating $(L_2-L_1)/L_1$, where $L_1$ is the length of segment AB, and $L_2$ is the length of segment A'B' which lies between the two center coordinates A' and B', and the lateral elongation rate PH is obtained by calculating $(H_2-H_1)/H_1$, where $H_1$ is the length of segment AC, and $H_2$ is the length of segment A'C' which lies between the two center coordinate A' and C'.

In the next place, two LEDs 20 arranged at (n, 1) and (n, 2) are turned off, and at the same time two LEDs 20 arranged at (n-1, 2) and (n-2, 1) are turned on. The CCD camera 4 is then swung upwardly at an angle corresponding to the lattice interval, and three emitting LEDs arranged at (n-1, 1), (n-1, 2) and (n-2, 1) are image-sensed through a small region just above adjacent to the small region which is at the left end and lowermost portion of the windshield 3. The same actions are repeated until the camera 4 swings to an upper limit angle at the left limit angle.

Subsequently, the windshield 3 is anticlockwisely rotated on the vertical axis at an angel corresponding to the lattice interval, and at the same time the CCD camera 4 is swung to a direction of the lower limit angle at this condition. Then, three LEDs 20 arranged at (n', 1), (n', 2) and (n'-1, 1) are turned on by an order from the computer 11, and image-sensed. The same actions are repeated until the windshield 3 rotates to the right limit angle and the camera 4 swings to the upper limit angle at the right limit angle. The detection of optical distortion of the windshield 3 is completed by filing data concerning values of lateral and longitudinal distortion angles to the computer 11.

On the system 1 according to the invention, the distance between the camera 4 for the image sensing means and the LED plate 2 for the target means does not change depending on which group of three emitting LEDs (a target or an unit target) is image-sensed. Accordingly, if respective optical distortions of many small regions of the same windshield are detected, greater geometrical error arises between the distortion angles detected according to the present invention and according to Makiguchi et al. shown in FIG. 6, for a small region which is at farther away from the point 7. However, it is possible to evaluate optical distortion detected according to the present invention utilizing the discriminant functions proposed by Makiguchi et al., by correcting the error with the computer 11.

Figure 13:
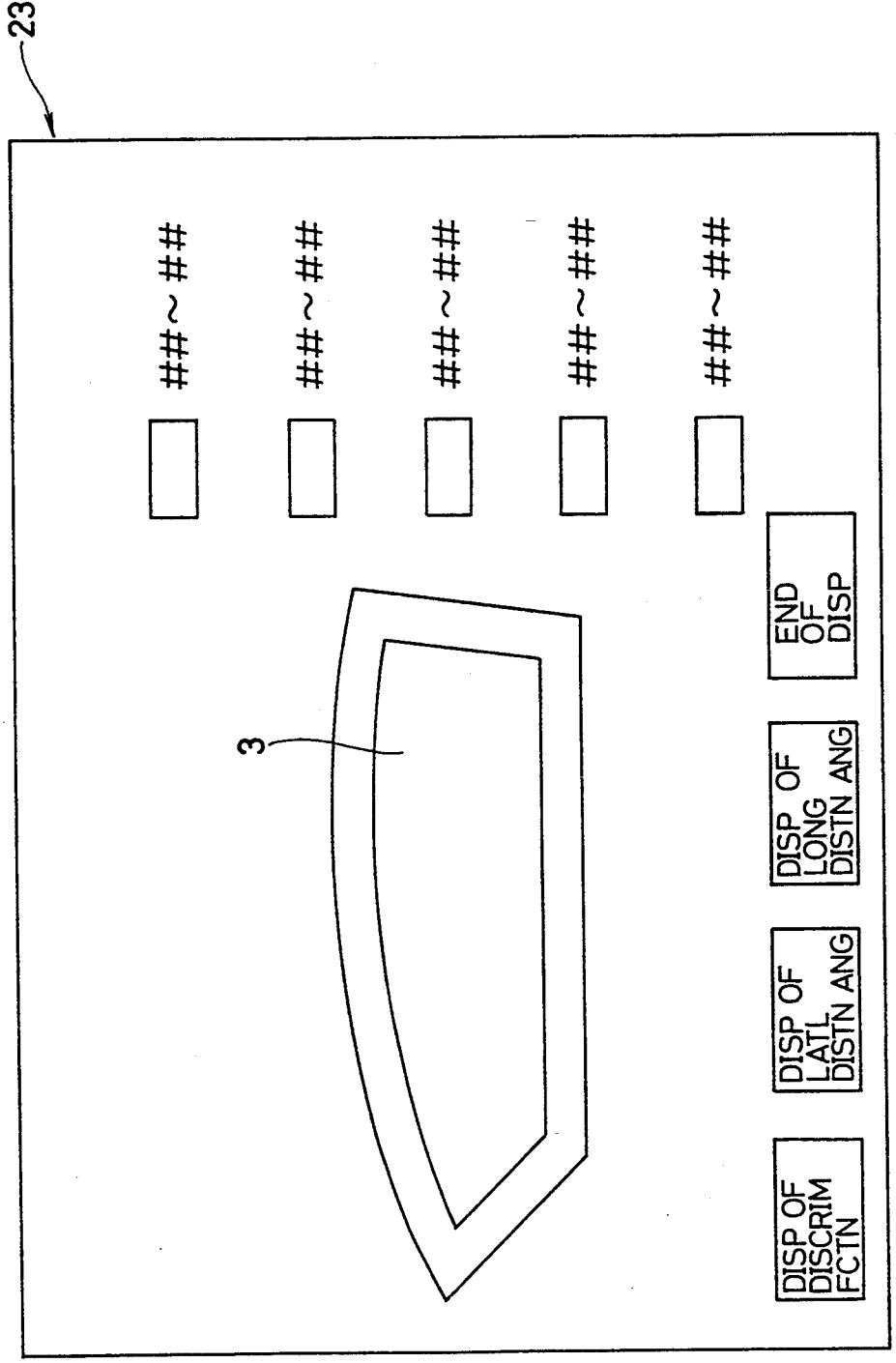
FIG. 13 is a front view of a CRT displaying a detected optical distortion.

Referring to FIG. 13, a picture of the CRT display 14 indicating a result of the detection acquired by above procedures is shown. The CRT display 14 should be a color display which can selectively indicate lateral distortion angles, longitudinal distortion angles or values of the discriminant functions calculated from the angles, by operating function keys. Those values are distinguished in colors with each suitable range, and substantially the overall region of the windshield 3 is indicated on the CRT 14. Furthermore, a printing which is the same to the picture indicated on the display 14 can be printed by the color printer 15, if desired.

Shown in FIG. 14 are distributions of optical distortion of the windshield 3, which are displayed as shown in FIG. 13 on the screen of a CRT. The optical distortion is represented with distortion angles: the longitudinal distortion-angle distribution and the lateral distortion-angle distribution are shown on the upper side and the lower side of FIG. 14, respectively.

The distributions are represented with the distortion angles in FIGS. 13 and 14, but can also be represented with elongation rates in addition to or in lieu of the distortion angles.

Figure 15:
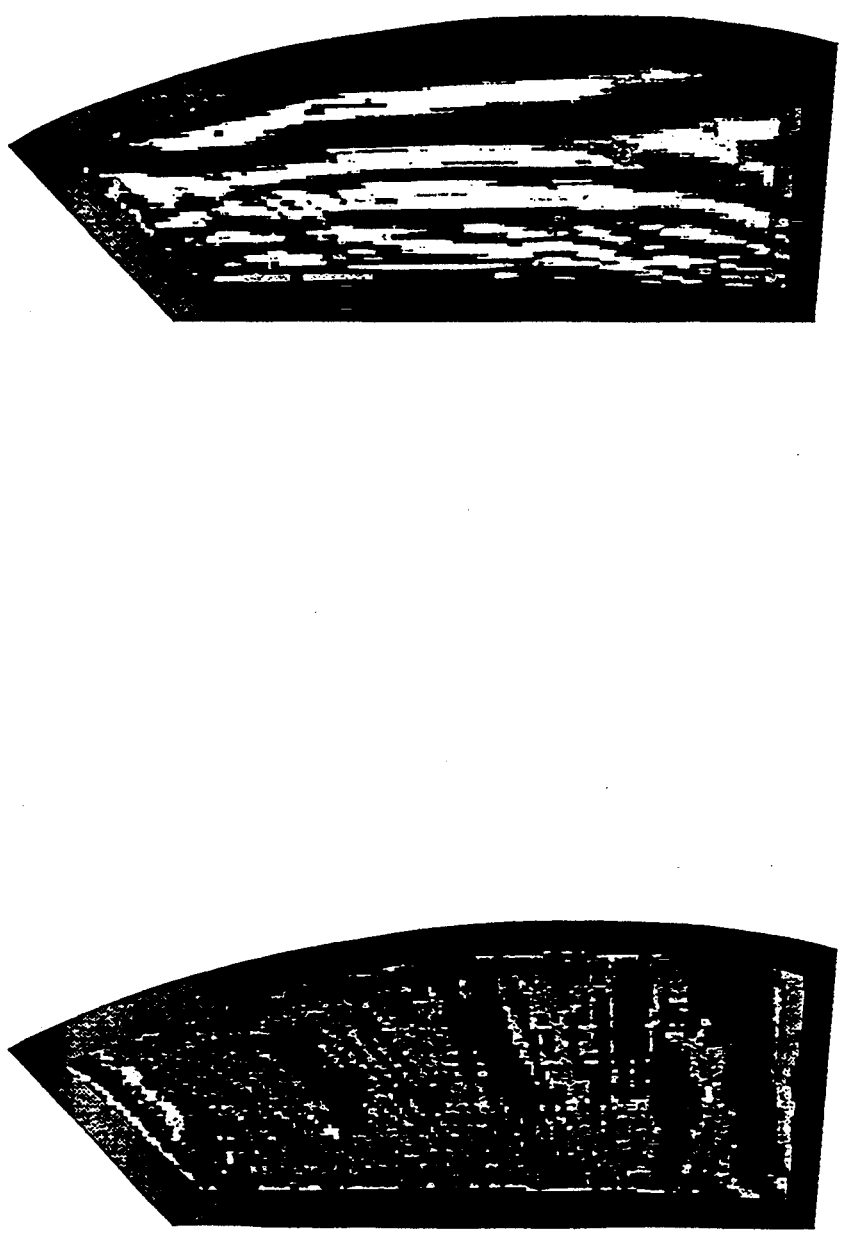
FIG. 15 is a distribution representation of optical distortion of a windshield, represented with longitudinal elongation rates and lateral elongation rates.

Shown in FIG. 15 are distributions of another optical distortion of the windshield 3, which are represented with the elongation rates: the longitudinal elongation-rate distribution and the lateral elongation-rate distribution are shown on the upper side and the lower side of FIG. 15.

Figure 16:
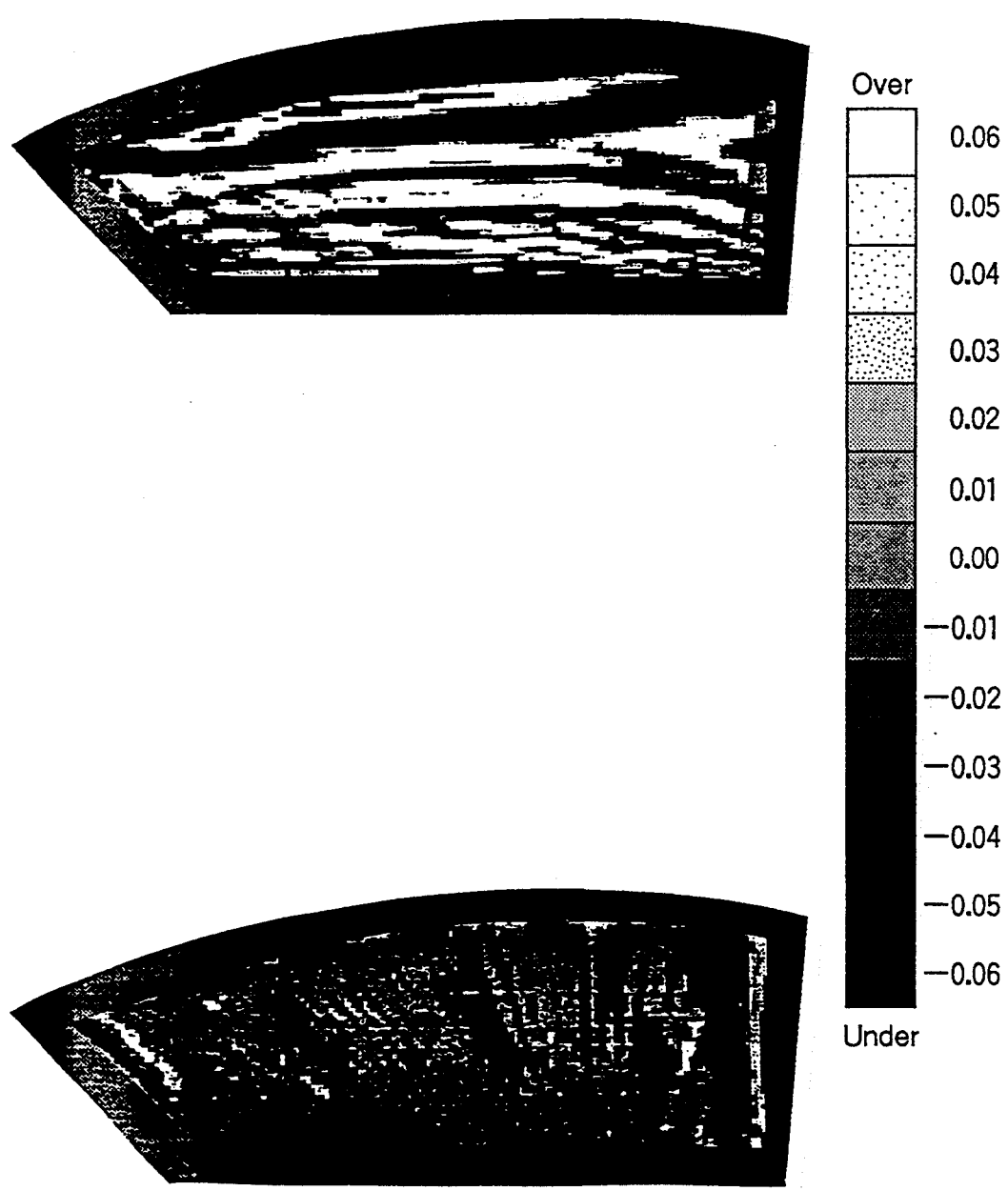
FIG. 16 is a distribution representation of optical distortion of a windshield, represented with longitudinal dioptres and lateral dioptres converted from longitudinal elongation rates and lateral elongation rates, respectively.

Moreover, in lieu of the elongation rates, the distribution can be represented with longitudinal dioptres and lateral dioptres that are obtained by converting the elongation rates to the dioptres (values obtained by correcting the elongation rates with respect to distance between the windshield 3 and the target, and size of the target image on the windshield 3). In FIG. 16, the longitudinal dioptre distribution is shown on its upper side, and the lateral dioptre distribution is shown on its lower side.

Figure 2:
FIG. 2 is an illustration for exemplifying a distribution of light parts and dark parts produced therein due to lens effect of a front windshield.
Figure 3A:
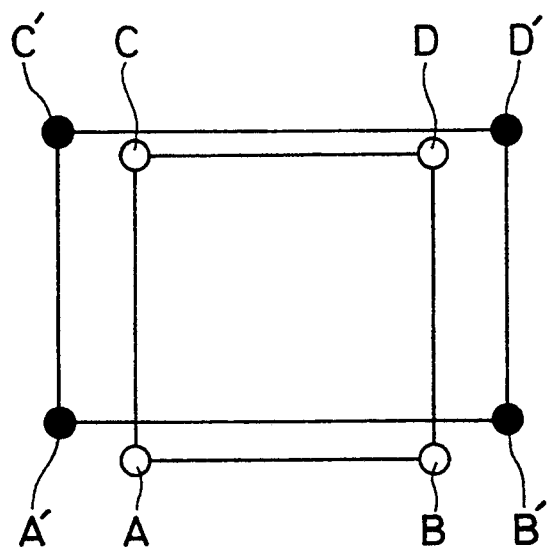
FIG. 3A is an explanatory drawing of optical distortion in a part of a front windshield where lens effect is invariably positive in a lateral direction.
Figure 3B:
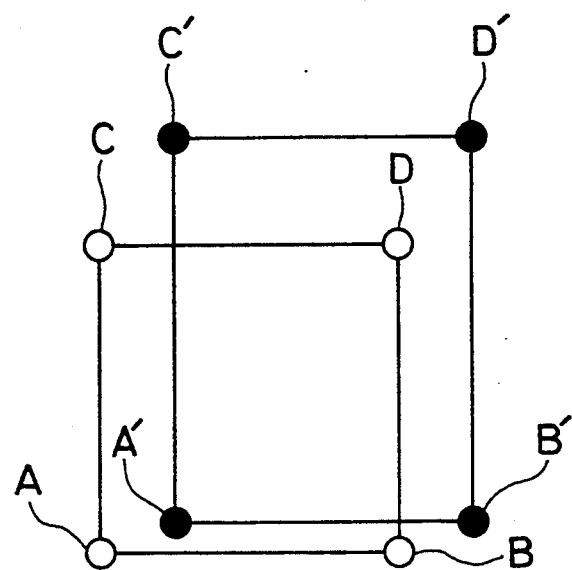
FIG. 3B is an explanatory drawing of optical distortion in a part of a front windshield where lens effect is invariably positive in a longitudinal direction.
Figure 4:
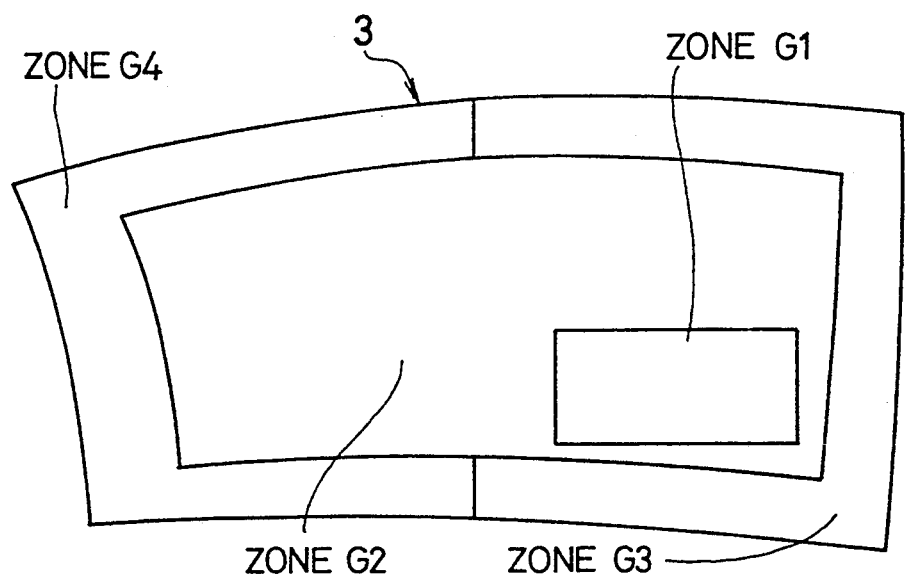
FIG. 4 is an explanatory drawing of divided observation zones of a front windshield, when it is viewed from an eye-point prescribed by JIS for a vehicle.
Figure 5:
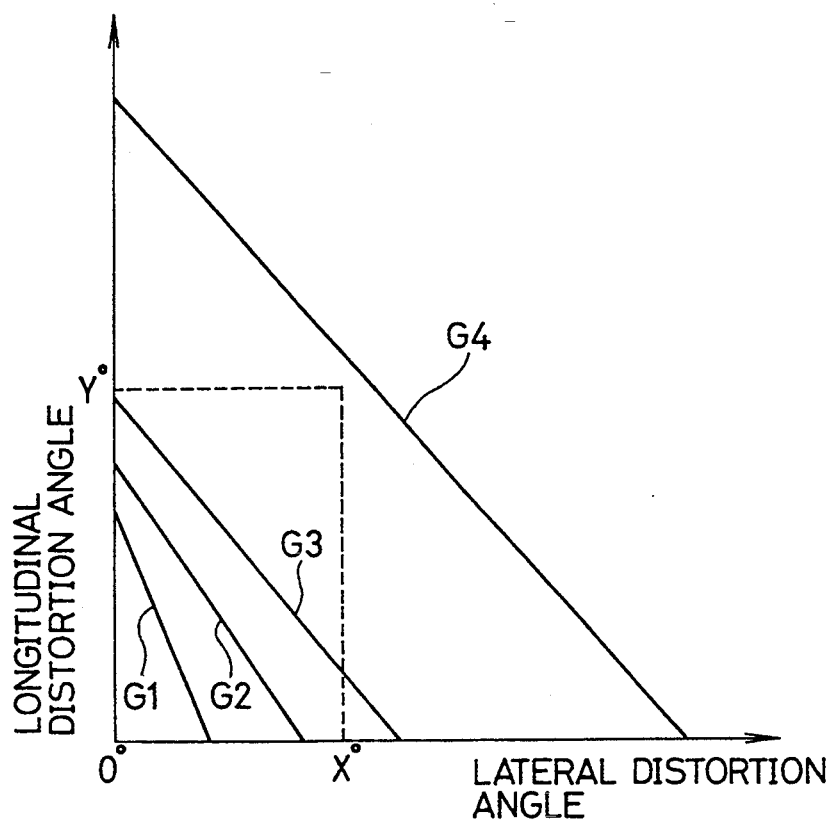
FIG. 5 is a graphical representation of discriminant functions given with each observation zone of FIG. 4.

In FIG. 14-16, the optical distortion of the windshield 3 is quantitatively shown, while in FIG. 2, it is qualitatively done.

Figure 17:
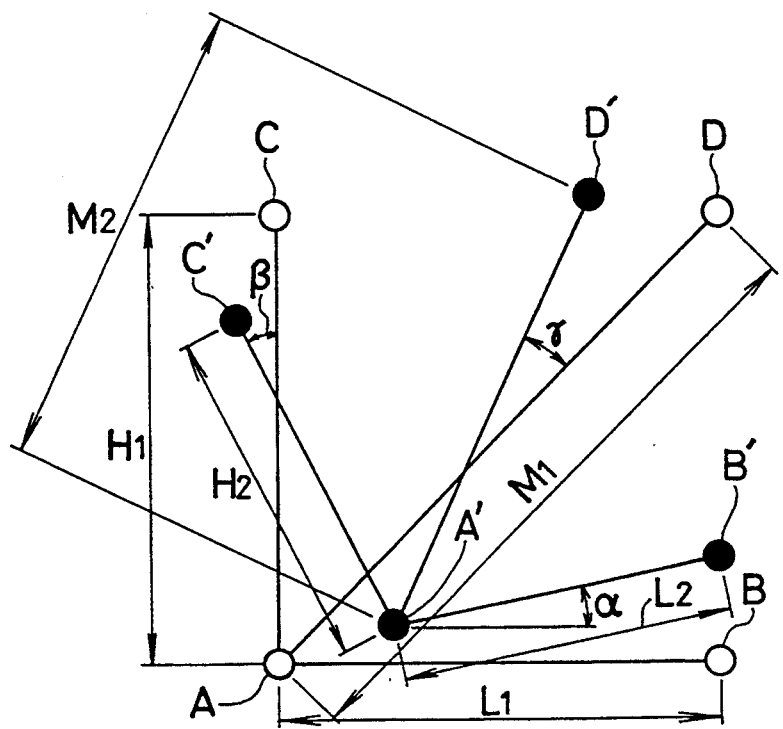
FIG. 17 is an explanatory Figure, corresponding to FIG. 1, of another system of detecting optical distortion of a plate-like member, which embodies the present invention and differs from the system shown in FIGS. 7–16.

Shown in FIG. 17 is another embodiment of a system of detecting the optical distortion of the platelike member in accordance with this invention, and it differs from the embodiment shown in FIGS. 7-16. FIG. 17 corresponds to FIG. 1, and the embodiment shown in FIG. 17 is substantially the same as the one shown in FIGS. 7-16, excepting the following points.

In the embodiment shown in FIGS. 7-16, the unit target comprises the three LEDs 20, but in the embodiment shown in FIG. 17, the unit target comprises four LEDs 20: to be more concrete, four LEDs 20 located in positions (n, 1), (n, 2), (n-1, 1) and (n-1, 2) shown in FIG. 8B are made to emit in turn, where n is a natural number of 2-150. Thus, in the embodiment shown in FIG. 17, the unit target comprising four light-emitting spots (LEDs 20) arranged substantially in square shape number 149 in the longitudinal direction and 1 in the lateral direction, and each adjacent target holds two spots in common. Since the unit target includes segment AD extending in a diagonal direction, for example, in a direction of forming an angle of 45°, so that it becomes possible to obtain optical distortion along the diagonal direction by means of measuring angle $\gamma$ formed by segment AD with segment A'D' that is observed through the platelike member. Further, it becomes possible to obtain an elongation rate along the diagonal direction by means of calculating $(M_2 - M_1)/M_1$, where $M_1$ is the length of segment AD and $M_2$ is the length of segment A'D', and it is also possible to obtain a dioptre along the diagonal direction from the elongation rate.

The two embodiments teach that the time required per windshield so as to detect optical distortion thereof is considerably more shortened than usual. Further, in the previously proposed method shown in FIG. 6, it is necessary to secure the platelike member, such as the windshield, to the automobile etc. in a state of practical use, to take photographs, and to enlarge the photographs to read distortion angles, but in this invention, they are not necessary at all and it is possible to detect the optical distortion of the platelike member in a short period of time and with high accuracy, so that such a platelike member as to produce comparatively large optical distortion can previously be rejected before it is actually incorporated.

Moreover, the unit target may comprise three or four light-emitting spots positioned in predetermined relationship with one another, so that light emitting elements, such as LEDs, can simply be used for the target, and images of the target are accurately and surely obtained by image sensing means.

Figure 6:
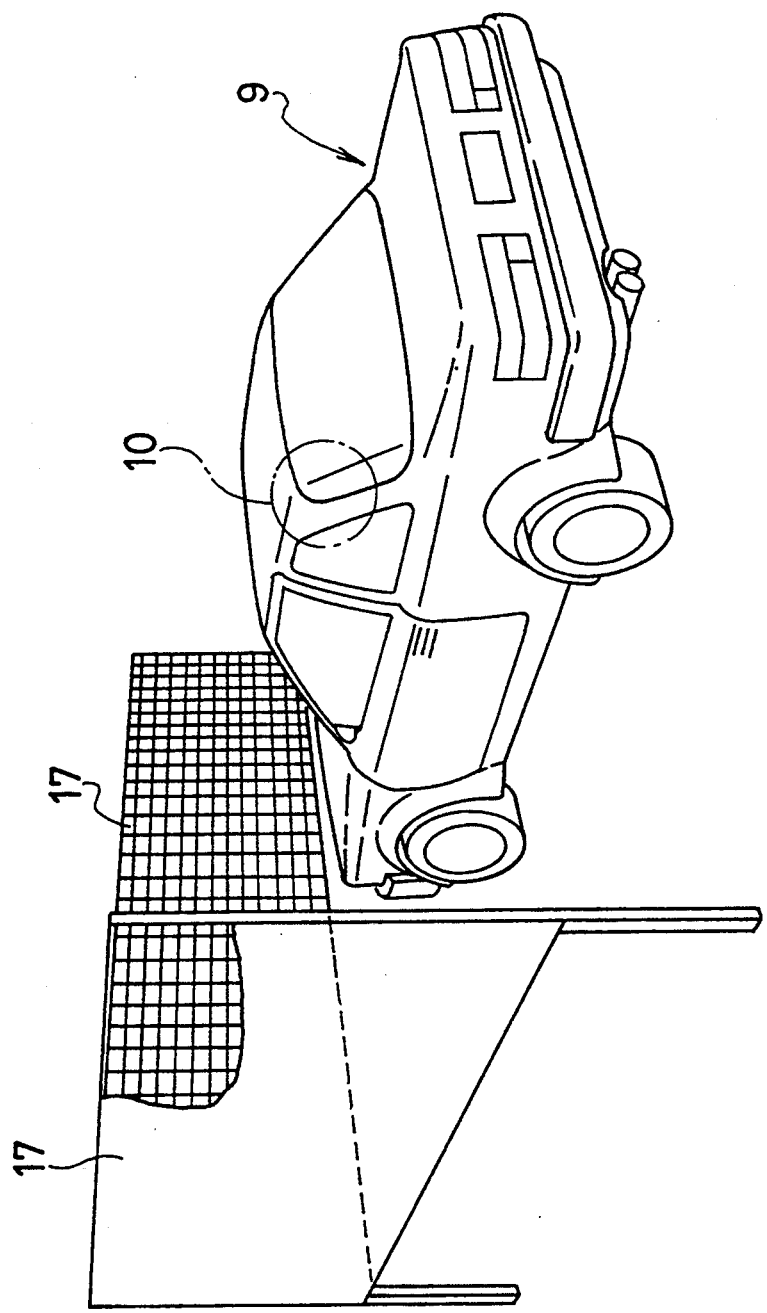
FIG. 6 is a perspective view of a previously proposed system of detecting optical distortion of a windshield.

In the previously proposed method shown in FIG. 6, it is necessary for the automobile to be surrounded by the panel having the lattice-like pattern that comprises many lines crossing perpendicularly to one another, but in this invention, no panel is used, so that it is not necessary to provide a large space in order to detect the optical distortion of the platelike member.

Furthermore, the unit target comprises three light-emitting spots arranged substantially in the shape of an isosceles triangle or four light-emitting spots arranged in the shape of a square, so that it is easy to deal with image signals obtained from the image sensing means.

When the image is sensed by the image sensing means, only the light-emitting spots belonging to one of the plurality of unit targets are emitted, so that it is prevented to be erroneously detected, and it becomes possible to deal with the image signals, which are obtained from the image sensing means, in high reliability.

The image processor serves to control changes of relative relationships of the positions among the image sensing means, the target and the plate-like member and to deal with the image signals obtained from the image sensing means in order to detect the optical distortion, so that it becomes possible to detect the optical distortion of the platelike member in a shorter period of time and with higher accuracy.

Moreover, the image processor includes means for converting the image signals, which are obtained from the image sensing means, to center coordinates obtained from the three or four light-emitting spots of the target, respectively, so that the accuracy of detecting the optical distortion of the platelike member can be much improved.

Having described specific preferred embodiments of the present invention with reference to the accompanying drawings, it is to be understood that the invention is not limited to those precise embodiments, and that various changes and modifications, for example, described below may be effected therein by one skilled in the art without departing from the scope or spirit of the invention as defined in the appended claims.

For example, in the above embodiments, the swing $\underline{a}$ of the CCD camera 4 and the rotation $\underline{b}$ of the windshield 3 may naturally be detected in reverse sequence. In other word, optical distortion of the windshield 3 can be detected by repeating procedures that fixing the camera 4 without swinging $\underline{a}$, rotating the windshield 3 from the left limit angle to the right limit angle together with image-sensings, and swinging the camera 4 at an angle corresponding to the lattice interval.

In the embodiments, though the plenty of LEDs 20 are arranged in the longitudinal direction in the LED plate 2, they may be arranged in the lateral direction. At that time, the CCD camera 4 is swung in the horizontal plane on the vertical axis, and the windshield 3 is rotated in the vertical plane on the horizontal axis.

Still furthermore, though the swing $\underline{a}$ and the rotation $\underline{b}$ are intermittenly performed at an angle corresponding to the lattice interval and image-sensed at stopping in the embodiments, the swing $\underline{a}$ and the rotation $\underline{b}$ may be continuously performed and image-sensed at every predetermined time.

In the above embodiments, the swing $\underline{a}$ of the CCD camera 4 and the rotation $\underline{b}$ of the windshield 3 are performed in the different directions, respectively, but if predetermined LEDs 20 can be sensed in turn through every small regions of the windshield 3 by the CCD camera 4, the relative positions among the CCD camera 4, the windshield 3 and the LED plate 2 may be changed in other ways: to be more concrete, only the windshield 3 is rotated both in a vertical direction and in a horizontal direction on the point 7 corresponding to the eye point, and the CCD camera 4 and the LED plate 2 comprising only three or four LEDs 20 located in predetermined relationships to one another are fixed. In another way, the CCD camera is swung both in a vertical direction and in a horizontal direction on the point 7 corresponding to the eye point, the windshield 3 is fixed, and the LED plate 2 comprising only three or four LEDs 20 located in predetermined relationships to one another is moved both in a vertical direction and in a horizontal direction so as to match the swing of the CCD camera 4.

Moreover, the swing $\underline{a}$ of the CCD camera 4 and the rotation $\underline{b}$ of the windshield 3 are performed in the same manner as to be describe above, and the LED plate 2 is moved in a vertical direction so as to match the swing of the CCD camera 4. In that event, it is enough if the LED plate even has only three or four LEDs 20 located in predetermined relationships to one another.

From the standpoint of preventing the erroneous detection, the light emitting element (LED 20) is used as the target in the above embodiments, but the LEDs may be replaced by non light-emitting marks which can be image-sensed by the camera 4, for example marks which are formed at intersections of the lattice-like straight lines pattern.

The optical distortion of any platelike member having the quality of being transparent, translucent or so can be detected by the system according to the present invention, besides the windshield of the automobile.

What is claimed is:

1. A system for detecting an optical distortion of a light-transmitting plate-like member, a predetermined region of the member being divided into a plurality of small parts, a target being sensed in turn through each small part of the region, the system comprising:
    target means having at least one target that has at least three light emitting points capable of representing at least one predetermined angle;
    image sensing means for sensing the target through each of the small parts of the region so as to determine the optical distortion of each of said small parts;
    position change means for changing a positional relationship among the image sensing means, the target and the plate-like member so as to position each of the small parts of the region between the image sensing means and the target sensed by the image sensing means and;
    control means connected to the target means the position means and the image sensing means for coordinating a timing of positioning each of said small parts with respect to the target means and the image sensing means and for timing an activation of the light emitting points and the image sensing means.

2. The system according to claim 1, wherein the plate-like member is a front windshield of a vehicle, and the position change means changes the relationship of the relative positions in a state that the image sensing means is kept substantially constant in a position corresponding to an eye-point prescribed by the Japanese Industrial Standards for the vehicle.

3. The system according to claim 1, wherein the predetermined angle represented by the three light emitting points of the target is substantially a right angle.

4. The system according to claim 1 wherein the target means comprises a plurality of targets, each of which has at least three light emitting points, and when one target is being sensed by the image sensing means, only the light emitting points of the target to be sensed are made to emit.

5. The system according to claim 1, wherein the optical distortion comprises at least one distortion angle with respect to at least one segment each represented by two of at least three light emitting points.

6. The system according to claim 5, wherein at least one distortion angle comprises a longitudinal distortion angle and a lateral distortion angle.

7. The system according to claim 1, wherein the optical distortion comprises at least one elongation rate with respect to at least one segment each represented by at least three light emitting points.

8. The system according to claim 7, wherein at least one elongation rate comprises a longitudinal elongation rate and a lateral elongation rate.

9. The system according to claim 8, wherein the target has four light-emitting points arrayed in the shape of a quadrilateral and at least one elongation rate further comprises an elongation rate with respect to a segment extending in a diagonal direction.

10. The system according to claim 1, wherein the optical distortion comprises both the distortion angle and the elongation rate.

11. The system according to claim 1, wherein processing means is provided to control the change of the relative positions by the position change means, and to process image signals from the image sensing means in order to sense the optical distortion.

12. The system according to claim 11, wherein the processing means includes means for converting the image signals into center coordinates specifying the at least three light emitting points, respectively.

13. A system for detecting an optical distortion of a light-transmitting plate-like member, a predetermined region of the member being divided into a plurality of small parts, a target being sensed in turn through each part of the region, the system comprising:
    target means having an array of unit targets in a substantially predetermined direction, each of said unit targets representing at least one predetermined angle;
    image sensing means for sensing one of the unit targets through one of the small parts of the region; and
    position change means for placing each of said small parts of the region between the image sensing means and one of the unit targets, which is to be sensed by the image sensing means, the position change means causing the image sensing means to swing substantially along the predetermined direction of the array of the unit targets, the position change means also causing the plate-like member to rotate along a plane substantially perpendicular to the predetermined direction; and control means connected to the target means, the position means and the image sensing means for coordinating a timing of positioning each of said small parts with respect to the target means and the image sensing means and for timing an activation of the light emitting points and the image sensing means.

14. The system according to claim 13, wherein the plate-like member is a front windshield of a vehicle, and the image sensing means is made to swing on an axis substantially perpendicular to the predetermined direction and substantially through a position corresponding to an eye-point prescribed by the Japanese Industrial Standards for the vehicle, and the platelike member is made to rotate on an axis substantially passing through the position corresponding to the eye-point and extending substantially in parallel with the predetermined direction.

15. The system according to claim 13, wherein the unit target comprises at least three light emitting points capable of representing at least one right angle substantially.

16. The system according to claim 13, wherein only a unit target to be sensed is made to emit light when the image sensing means is put in action.

17. The system according to claim 13, wherein the optical distortion comprises at least one distortion angle with respect to at least one segment each represented by two of at least three light emitting points.

18. The system according to claim 17, wherein at least one distortion angle comprises a longitudinal distortion angle and a lateral distortion angle.

19. The system according to claim 13, wherein the optical distortion comprises at least one elongation rate with respect to at least one segment each represented by two of at least three light emitting points.

20. The system according to claim 19, wherein at least one elongation rate comprises a longitudinal elongation rate and a lateral elongation rate.

21. The system according to claim 20, wherein the unit target has four light-emitting points arrayed in the shape of a quadrilateral and at least one elongation rate further comprises an elongation rate with respect to a segment extending in a diagonal direction.

22. The system according to claim 13, wherein the optical distortion comprises both the distortion angle and the elongation rate.

23. The system according to claim 13, wherein processing means is provided to control the swinging action of the image sensing means and the rotating action of the platelike member that are caused by the position change means, and to process image signals from the image sensing means in order to sense the optical distortion.

24. The system according to claim 23, wherein the unit target comprises at least three light emitting points capable of representing a right angle, and the processing means includes means for converting image signals into center coordinates respectively specifying the at least three light emitting points.

* * * * *